(12) United States Patent
Zhang et al.

(10) Patent No.: US 6,174,531 B1
(45) Date of Patent: Jan. 16, 2001

(54) METHODS OF PREPARATION OF BIOGINKGO

(75) Inventors: De Cheng Zhang; Zhanghun Yu, both of Shanghei (CN); Raymond Cooper, Los Altos; Michael Chang, Thousand Oaks, both of CA (US)

(73) Assignee: Pharmanex Inc., Redwood City, CA (US)

( * ) Notice: Under 35 U.S.C. 154(b), the term of this patent shall be extended for 0 days.

(21) Appl. No.: 09/198,100

(22) Filed: Nov. 23, 1998

Related U.S. Application Data

(60) Provisional application No. 60/066,867, filed on Nov. 25, 1997.

(51) Int. Cl.$^7$ .......................... A61K 35/78; A61K 31/70; A01N 43/04
(52) U.S. Cl. ........................................... 424/195.1; 514/27
(58) Field of Search .............................. 424/195.1; 514/27

(56) References Cited

U.S. PATENT DOCUMENTS

| | | | |
|---|---|---|---|
| 4,683,140 | * 7/1987 | Kang | 426/489 |
| 4,892,883 | 1/1990 | Chatterjee et al. | 514/464 |
| 5,089,636 | * 2/1992 | Kwak et al. | 547/297 |
| 5,128,131 | 7/1992 | Motoyama et al. | 424/195.1 |
| 5,158,770 | 10/1992 | Saito et al. | 424/195.1 |
| 5,178,735 | 1/1993 | Manabe et al. | 203/49 |
| 5,322,688 | 6/1994 | Schwabe | 424/195.1 |
| 5,376,371 | 12/1994 | Bombardelli | 424/195.1 |
| 5,389,370 | 2/1995 | O'Reilly et al. | 424/195.1 |
| 5,399,348 | * 3/1995 | Schwabe | 424/195.1 |
| 5,468,492 | 11/1995 | Szaloki et al. | 424/195.1 |
| 5,512,286 | * 4/1996 | Schwabe | 424/195.1 |
| 5,637,302 | 6/1997 | Bombardelli et al. | 424/195.1 |
| 5,660,832 | 8/1997 | Steiner et al. | 424/195.1 |
| 5,700,468 | 12/1997 | Bombardelli et al. | 424/195.1 |
| 5,730,987 | 3/1998 | Omar | 424/195.1 |

OTHER PUBLICATIONS

Chemical Abstr. vol. 122, No. 21, Nov. 22, 1995, p. 674, col. 1, the abstract No. 261362r, Sung, S.H. et al. 'Seasonal and sexual variation of ginkgolides contends in ginkgo leaves.' Yakhak Hoechi 1994, 38(1), 20–3 (Korean).

* cited by examiner

*Primary Examiner*—Christopher Tate
(74) *Attorney, Agent, or Firm*—Jeffer, Mangels, Butler & Marmaro LLP

(57) ABSTRACT

The invention relates to a novel process for producing novel extracts of *Ginkgo biloba* leaves. The invention further relates to a process which produces novel extracts of *Ginkgo biloba* with an increased amount of one of the major lactones and having an improved biological activity. Further, the disclosed process allows for a controlled method to produce a desired ratio of flavone glycosides to lactones in the end product. The invention also discloses new extracts from *Ginkgo biloba*, particularly for oral application.

12 Claims, 1 Drawing Sheet

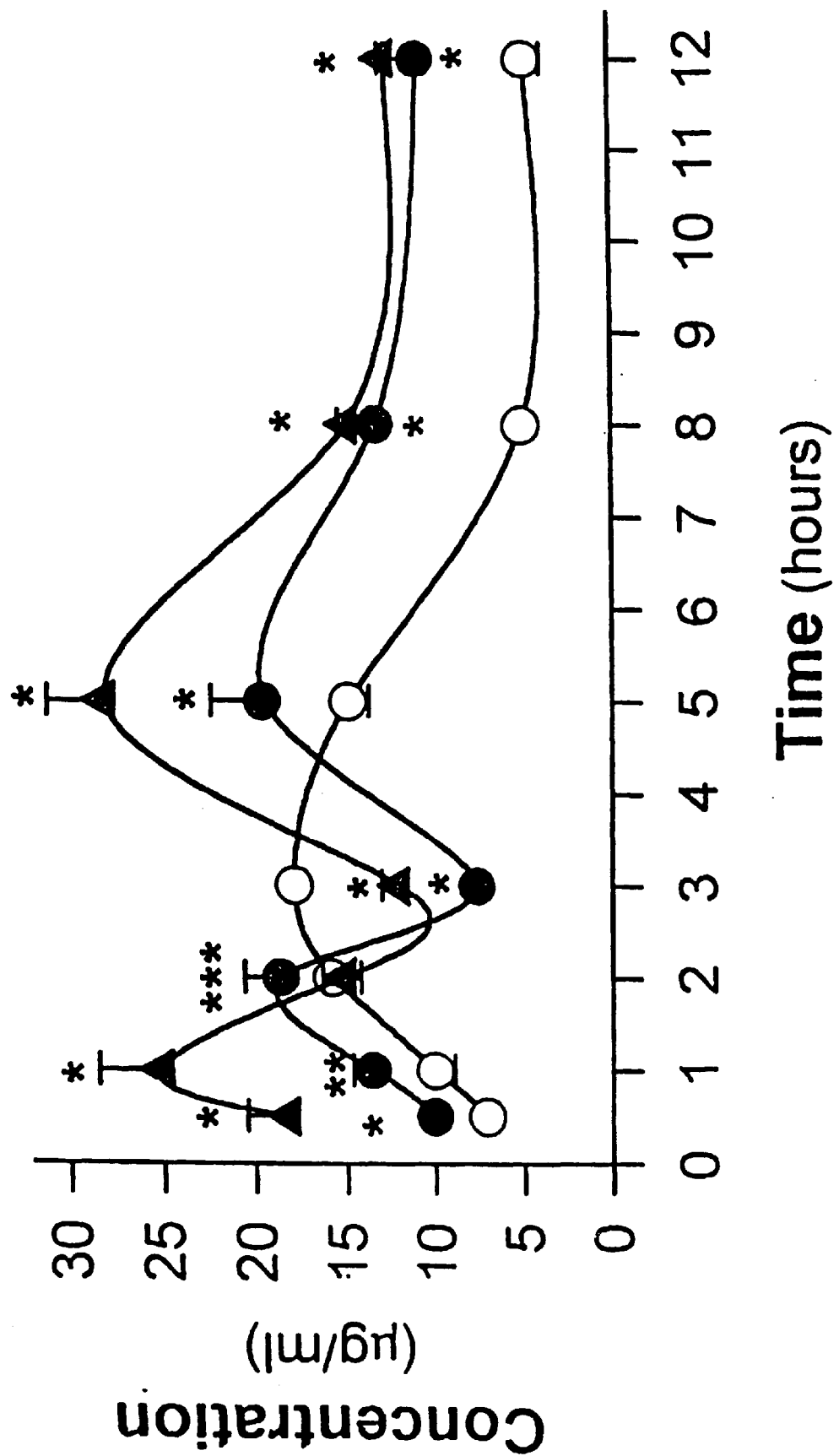

METHODS OF PREPARATION OF BIOGINKGO

This application claims the benefit of U.S. Provisional Patent Application Ser. No. 60/066,867, filed Nov. 25, 1997, the disclosure of which is incorporated herein by reference.

FIELD OF THE INVENTION

The present invention encompasses a novel process for producing extracts of *Ginkgo biloba* leaves. The invention particularly relates to a process leading to new chemical compositions useful for therapeutic purposes. More particularly, the invention relates to *Ginkgo biloba* extracts containing an increased concentration of a major endogenous lactone normally found in such leaves and shows improved biological activity. Further, the processes of the invention allow for control over the ratio of flavone glycosides to lactones in the final composition.

BACKGROUND OF THE INVENTION

*Ginkgo biloba* is one of the oldest species in the world, and is considered a living fossil. Zhongliang, Chin. Pharm J. 1996, 31:(6) 326–331. It is indigenous to China, although now it has been introduced and cultured in most places in the world. The mature seeds are edible and are used as one of the traditional Chinese medicines. The chemical constituents of Ginkgo leaves are characterized by the presence of diterpene (sesquiterpene) lactones, and flavonoid glycosides as active principles, and ginkgolic acids as toxic substances in the *Ginkgo biloba* extract (GBE). Some of the above mentioned compounds are used as reference substances in qualitative and quantitative analysis of GBE. Ginkgolides A, B, C are diterpene lactones; bilobalide is a sesquiterpene lactone. The lactones are specific antagonists against platelet activating factors (PAF). Flavonoid glycosides are thought to have many useful biological activities including the activities of dilating coronary vessels, improving peripheral and brain blood circulation, and preventing intravascular thrombogenesis. For example, extracts from the leaves of the *Ginkgo biloba* tree (maidenhair tree) have been used for many years in the treatment of patients with conditions related to aging (DeFeudis, F. G., (1991) *Ginkgo biloba* extract. (EGb 761): Pharmacological activities and clinical applications. Editions Scientifiques Elsevier, Paris; Kleijnen, J., Knipschild, P. (1992) Lancet 340, 1136–1139). These conditions include cerebral insufficiency, which is defined by a group of symptoms exemplified by problems with short-term memory and concentration, lack of energy, tinnitus, headache, and depression (Kleijnen, J., Knipschild, P. (1992) *Br. J. Clin. Pharmacol.* 352–358). The most important active ingredients of the extracts are thought to be the flavonoids and the terpenoids, whereas ginkgolic acids are believed to cause contact dermatitis and other toxicities.

Ginkgo extracts are usually standardized in terms of their flavonoid glycoside and terpene lactone (ginkgolides and bilobalide) content (Sticher, O. (1993) *Planta Med.*, 59, 2–11; Stinke, B., Muller, B., Wagner, H. (1993) *Planta Med.* 59, 155–160). Methods of preparing active extracts of *Ginkgo biloba* have been described in the art.

U.S. Pat. No. 5,637,302 is directed to a process where the lipophilic substances are removed from the extracts of *Ginkgo biloba* leaves using n-hexane, n-heptane or a solvent comprising a major proportion of toluene and a minor proportion of n-butanol. The resultant compositions (extracts) are disclosed as containing 22–26% flavone glycosides and 2.5–4.5 weight percent each of ginkgolides and bilobalide.

U.S. Pat. No. 5,512,286 is directed to extracts of *Ginkgo biloba* free of serum precipitating and/or hemagglutinating properties. The leaves are extracted using an aqueous acetone or alkanol (with 1–3 carbon atoms) or anhydrous methanol, precipitating out the lipophilic components, adding ammonium sulfate and extracting with methyl ethyl ketone, a multi-step extraction with water-immiscible butanol or pentanol (or, alternatively, with lead salts), alcohol extractions and column chromatography using a polyamide, or preferably a cross-linked polyvinyl pyrrolidone substitute.

Similarly, U.S. Pat. No. 5,399,348 describes extracts of *Ginkgo biloba* where the leaves are extracted using an aqueous acetone or alkanol (with 1–3 carbon atoms) or anhydrous methanol, precipitating out the lipophilic components, adding ammonium sulfate and extracting with methyl ethyl ketone, diluting in an aqueous alcohol solution which is treated with a lead salt or insoluble polyamide and extracting with an aliphatic or cycloaliphatic solvent.

EP-A 0 324 197 describes a method for the preparation of an extract from *Ginkgo biloba* leaves in which an aqueous solution of a lower alcohol or ketone, obtained after extraction of the leaves, is concentrated in the presence of kieselguhr. The resultant aqueous suspension is filtered through kieselguhr, the filtrate is extracted with butanone and the extract is freed from the solvent.

EP-A 330 567 relates to a method for the preparation of an extract from *Ginkgo biloba* leaves in which the crushed leaves are extracted with an aqueous ketone compound. This extract is concentrated until biflavones and hydrophobic compounds precipitate. After filtration the aqueous concentrate is rendered alkaline, whereby the proanthocyanidins precipitate. After separation of the precipitate and acidification of the filtrate, a liquid-liquid-extraction is carried out with a $C_{4-6}$-ketone compound in the presence of ammonium sulfate. The extract is obtained after stripping of the ketone compound.

The extracts from *Ginkgo biloba* leaves prepared by the methods in DE-B 17 67 098 and DE-B 21 17 429 are disclosed as being substantially free of alkylphenol compounds due to removal of the lipophilic components by a liquid-liquid extraction of the aqueous acetone extract with a substantially water-immiscible lipophilic solvent, e.g. with a chlorinated aliphatic lower hydrocarbon such as carbon tetrachloride. However, while the content of flavone glycosides is increased from 3 to 4% in the crude extract to approximately 24% in the final product, in this step, the therapeutically valuable ginkgolides and the bilobalide are considerably reduced so that their content in the final product in Example 1 of DE-B 21 17 429 is a maximum of 0.5% in the case of ginkgolides A, B, C, and J in total and approximately 0.3% in the case of bilobalide. Also, chlorinated aliphatic hydrocarbons are associated with certain toxicities and are generally undesirable.

U.S. Pat. No. 5,399,370 is directed to extracts of *Ginkgo biloba* having 40–60% flavone glycosides, 5.5–8.0% ginkgolides and 0.5–7.0% bilobalides. The method involves extraction with either aqueous alkanol or acetone or anhydrous methanol, precipitating out the lipophilic components, extracting with an ester of formic acid or acetic acid, and an additional extraction with a butanol or pentanol. Activated carbon may also be used to remove certain substances prior to the ethyl acetate or ester extraction.

The Ginkgo extract used most frequently at present for therapeutic purposes (tanakan$^R$; roekan$^R$ or tebonin$^R$; "EGb 761") contains, besides 24% flavone glycoside compounds, 6% terpene lactone compounds; see K. Drieu, *La Presse Medicale* Vol. 15 (1986), 1455–1457. These are the ginkgolides A, B, C and J as well as the bilobalide, which makes up approximately half of the 6%. The content of ginkgolide B found in currently available preparations ranges from about 0.88% to about 1.3%. The therapeutic daily dosage is 120 mg.

EP-A-86 315 describes a method of reducing the content of polymeric polyphenol compounds in the extracts by means of polyvinyl pyrrolidone in ethanolic-aqueous solution.

U.S. Pat. No. 4,981,688 discloses a method for extraction of *Ginkgo biloba* involving extraction from the leaves using an aqueous ketone solvent; concentration of the extraction liquors in order to precipitate the biflavonoids and the hydrophobic substances; alkalinization of the filtrate so as to precipitate the proanthocyanidins; acidification of the filtrate; liquid-liquid extraction of the filtrate with a $C_4$–$C_6$ ketone in the presence of ammonium sulfate; and recovery of the extract by taking the ketone phase to dryness.

Flavones have also been extracted from *Ginkgo biloba* leaves with boiling water and an absorbent resin identified as being manufactured by Tianjing Gel Factory Model No. D1010. Xino et al., (1990) Chinese J. of Pharmaceuticals 21 (8): 340–341.

Other extracts of *Ginkgo biloba* and methods for their preparation are disclosed, for example, in U.S. Pat. Nos. 5,637,302; 5,700,468; 5,660,832; 5,158,770; 5,128,131; and 4,892,883.

Notwithstanding the numerous patents and publications concerning extractions of processes for *Ginkgo biloba*, there exists a need for processes which are free from toxic solvents, are relatively inexpensive and which further can be used to produce compositions with superior bioavailability.

SUMMARY OF THE PREFERRED EMBODIMENTS

In accordance with one aspect of the present invention, there is provided a process for the production of an extract from leaves from *Ginkgo biloba* which includes the steps of collecting green *Ginkgo biloba* leaves during the months of August through October; extracting at least one lactone and at least one flavone glycoside from the leaves; and combining the at least one lactone and the at least one flavone glycoside.

According to another aspect of the present invention, there is provided a process for the production of an extract from leaves from *Ginkgo biloba* which includes the steps of extracting at least one lactone and at least one flavone glycoside from the leaves using column chromatography, and combining the at least one lactone and the at least one flavone glycoside to form an extract, wherein the extract contains less than about 5 ppm of ginkgolic acids.

According to an additional aspect of the present invention, a process for the production of an extract from leaves from *Ginkgo biloba* includes the steps of extracting a plurality of flavone glycosides and a plurality of lactones from the leaves using column chromatography, the lactones including ginkgolide A, ginkgolide B and ginkgolide C; and combining the flavone glycosides and the lactones to form an extract containing about 22 wt % to 27 wt % flavone glycosides and about 5 wt % to 7 wt % lactones.

Preferably the ratio of the amount of ginkgolide B to the sum of the amounts of ginkgolide A and ginkgolide C in the extract is about 1.4:5% to about 1.5:7%.

According to still another aspect of the present invention, a process for the production of an extract from leaves of *Ginkgo biloba* includes the steps of preparing a crude extract containing at least about 3 wt % of flavone glycosides by extracting the leaves in an alcohol solution; filtering and concentrating the crude extract; diluting the concentrated crude extract with boiling water and precipitating the extract; removing water-insoluble lipophilic components from the extract; performing column chromatography on the extract and eluting the column with a gradient elution of about 5% to about 75% alcohol solution, whereby a plurality of alcohol fractions containing flavone glycosides and lactones is obtained; and combining the flavone glycosides and lactones from the alcohol fractions to afford an extract having a specified concentration of each of the lactones and flavone glycosides.

According to still another aspect of the present invention, a process for the production of an extract from the leaves of *Ginkgo biloba* includes the steps of extracting fresh or dried leaves from *Ginkgo biloba* which are crushed to a pore size of about 5–20 mesh powder using about 50% alcohol solution to yield a crude extract comprising at least about 5 wt % of flavone glycosides; filtering and concentrating the crude extract to a density of about 1.2 to 1.25 g/cm$^3$; diluting the concentrated crude extract with boiling water and precipitating the diluted extract for about 24–48 hours at about 10°–12° C.; removing water-insoluble lipophilic components from the diluted extract by high speed tubular centrifuge at a rotary speed of approximately 16,000–20,000 r/min; performing column chromatography on the centrifuged extract using a column packed with 14–30 or 30–60 mesh polyamide in about 95% alcohol solution; eluting the column with a gradient elution of an about 5% to an about 75% alcohol solution; obtaining lactones in the recovered 10–20% alcohol fractions by first concentrating the lactones, then extracting the lactones with ethyl acetate, and subsequently determining the concentration of the recovered lactones; obtaining flavone glycosides in the recovered 20–75% alcohol fractions and then determining the concentration of the recovered flavone glycosides; forming a combined extract by combining the recovered lactones and flavone glycosides to a selected concentration of each; and removing alkylphenol compounds, usually referred to as ginkgolic acids, from the combined extract to a residual content of less than about 5 ppm ginkgolic acids.

Extracts prepared according to the foregoing processes are also provided.

In accordance with still another aspect of the present invention, an extract of the leaves of *Ginkgo biloba* is provided which comprises about 27 wt % flavone glycosides and about 6–7 wt % lactones. The extract has a ginkgolide B content of at least about 1.40 wt %.

Pharmaceutical compositions including the foregoing extracts and a pharmaceutically acceptable carrier are also provided.

Dietary supplements including the foregoing extracts and a physiologically acceptable carrier, such as water, a food composition, and the like, are also provided.

Other objects, features and advantages of the present invention will become apparent to those skilled in the art from the following detailed description. It is to be understood, however, that the detailed description and specific examples, while indicating preferred embodiments of the present invention, are given by way of illustration and not limitation. Many changes and modifications within the scope of the present invention may be made without departing from the spirit thereof, and the invention includes all such modifications.

BRIEF DESCRIPTION OF THE DRAWINGS

The invention may be more readily understood by referring to the accompanying drawings in which FIG. 1 shows: Plasma ginkgolide concentration vs time curves for Ginkgo extracts. (—○—), control 24/6, 40 mg/kg; (—æ—), BioGinkgo 27/7, 40 mg/kg; (—■—) BioGinkgo 27/7, 60 mg/kg. Each point is the mean±SD for 8 rabbits. *, $p<0.001$; , $p<0.002$, *, $p<0.01$ vs. control 24/6 extract.

DETAILED DESCRIPTION OF THE PREFERRED EMBODIMENTS

The present invention has many advantages over the conventional or previously reported methods of extraction of Ginkgo biloba leaves including: 1) compositions can be prepared containing various ratios of flavones to lactones in a controlled setting and can even be prepared on one assembly line; 2) the process is free from toxic organic solvents; 3) the products produced by the novel processes of the invention have their natural proportion of active components, with almost no changes of ratio of main principles occurring during the process to obtain active principles; and 4) the process is adaptable to ginkgo leaves of variable quality to achieve the desired final product—which is an important consideration from the manufacturing standpoint. Thus, the process of the invention ensures a product of consistent quality, irrespective of the fact that the ginkgo leaves may vary in their chemical composition.

In one embodiment of the invention, dried and shredded green Ginkgo biloba leaves which have been specifically selected are extracted with ethanol. The extract is then concentrated and centrifuged to remove insoluble material. The concentrated extract is then loaded onto a polyamide (Nylon-6) 14–30 mesh gel absorption column. The column is first washed with deionized water followed by gradient elution with an aqueous ethanol mobile phase (from 5% to 75% ethanol). Eluent from approximately 5%, 10%, and 15% ethanol fractions are combined and concentrated to yield an aqueous solution. This aqueous solution is extracted twice with ethyl acetate and concentrated to yield an extract containing the lactones. Eluent from about 20% to 75% ethanol is combined and concentrated to yield an extract containing the flavone glycosides. The two extracts are combined, concentrated, and washed twice with hexane. After drying, the concentrated extract is solidified and pulverized to yield the desired product.

Once the desired product is obtained, it can be administered in various forms, such as pharmaceutical compositions and dietary supplements, by combining the product with appropriate vehicles. Pharmaceutical compositions will include pharmaceutically acceptable carriers, such as sterile saline or a solid composition suitable for tableting. Dietary supplements will include an appropriate physiologically acceptable carrier, such as a liquid base, a food item, and the like. Such compositions can readily be prepared by those skilled in the art.

Analytical systems for HPLC determination of flavonoids, lactones and ginkgolic acid are performed.

The quality of the Ginkgo leaves is strictly examined and the quality control in each step is checked. Thus, the degree of fragmentation is checked during cutting process, the density of fluid extract during concentration of the extract is checked, the transparency and the content of active constituents are tested before the centrifuged extract is applied to column chromatography, and the content of total flavonoid glycosides and total lactones are examined before the elimination of the ginkgolic acids. Further, reduction in the content of ginkgolic acids, as well as the ratio of active components reduction in e.g., flavonoids, terpene lactones, are determined as key indexes for quality control until the final product is formed.

The invention uses select Ginkgo biloba leaves to optimize the end product obtained according to the inventive process. Applicants have discovered that the quality of Ginkgo leaves varies when obtained from different origins, such as Taixing, Huifeng, Luyuan, Huayin, Huzhou, Jingzai, Pizhou and Tangcheng as well as when collected at different seasons. For example, leaves from the Shandong province of China have a relatively higher content of flavonoids. Also, the flavonoids in leaves vary greatly in different seasons, with leaves collected in August, September, and October being higher in flavonoids. In a preferred embodiment, the leaves of the invention are collected from August to September. Additionally, the green leaves of relatively young trees are preferred. In a preferred embodiment the leaves are picked from trees that are 3–5 years of age. Thus, the quality of Ginkgo leaves can enhance the yield of the GBE product.

A. METHOD OF DETERMINING QUALITY OF THE STARTING MATERIALS

In order to control water content in the leaves, green leaves are dried to a constant weight in a water detector such as the Kangle DZF-1 Model or in a constant temperature oven. The content of water in the leaves is then calculated. The content of water in the leaves is preferably less than about 8 weight percent.

In order to detect the active constituents, the green leaves are crushed to approximately 5–20 mesh powder. An approximately 40%–70% alcohol solution and preferably an approximately 50% alcohol solution is added and refluxed for 2 hours in an extraction apparatus. The crushed leaves are then filtered to a pore size of 120 mesh. The extraction is repeated in the alcohol solution and is then filtered at approximately 120 mesh. The two filtered solutions are combined and concentrated under a reduced pressure of approximately 0.08–0.09 Mpa at 70° C. to dry the extract. The crude extract should be greater than 25 percent weight. HPLC analysis is then performed to determine the content of total flavone glycosides in the crude extract by methods known in the art. One method, for example, is by using a Waters Novapak™ $C_{18}$ 3.9×150 mm column with an 0.04% phosphoric acid:methanol (51:49) eluent at a flow rate of 1 ml/min. UV detection is at 260 nm. The total glycoside content is preferably no less than 3 percent and typically approximately 5 percent weight.

TABLE 1

| Origin of Ginkgo leaves (See Section 5.1) | | yield (%) | content of flavones (%) | content of total lactone (%) | yield of transferring to GBE 27/7 |
|---|---|---|---|---|---|
| A | centrifugal liquid | 19.56 | 3.50 | 3.00 | |
|   | final products | 1.72 | 26.64 | 17.70 | 1.72 |
| B | centrifugal liquid | 23.69 | 3.00 | 2.60 | |
|   | final products | 1.64 | 35.32 | 21.80 | 2.14 |
| C | centrifugal liquid | 23.80 | 3.1 | 3.10 | |
|   | final products | 2.08 | 26.87 | 20.10 | 2.08 |

TABLE 1-continued

| Origin of Ginkgo leaves (See Section 5.1) | | yield (%) | content of flavones (%) | content of total lactone (%) | yield of transferring to GBE 27/7 |
|---|---|---|---|---|---|
| D | centrifugal liquid | 22.38 | 4.30 | 2.90 | |
| | final products | 2.18 | 38.66 | 21.70 | 3.12 |

B. EXTRACTION

Once it is determined that the raw material (leaves) is of a desirable quality, the selected leaves are extracted as described in section 5.2, above except that a third extraction is performed in the same manner as the second extraction. Also, leaves are crushed to a pore size of approximately 10–20 mesh powder. The extract is then concentrated by separating most of the organic solvent from the above filtration solution by evaporation or distillation under reduced pressure to form a high-density fluid extract (D=1.2–1.25 g/cm$^3$).

Applicants have discovered that the use of an alcohol solution (pharmaceutical industry grade solvents are used throughout unless otherwise indicated) is superior to the use of acetone.

C. REMOVAL OF THE WATER-INSOLUBLE LIPOPHILIC COMPONENTS THROUGH CENTRIFUGATION

The high-density fluid extract is diluted with boiling water (the amount of water will vary depending on the quality of Ginkgo leaves, so that more water is added when the amount and quality of the ginkgo leaves is high). For example, the high-density fluid extract of 100 kg ginkgo leaves is diluted with approximately 200–300 liters boiling water. The solution should be kept boiling and stirred constantly for about 20 minutes. The solution is then precipitated for about 24–48 hours at approximately room temperature. Preferably, the temperature is approximately 10–12° C. The water-insoluble lipophilic components are removed from the diluted aqueous solution by high speed tubular centrifuge (rotary speed 16,000–20,000 r/min).

D. COLUMN CHROMATOGRAPHY

1. Polyamide

Column chromatography is preferably performed using a stainless steel column where the ratio of the diameter of column to the length of column is approximately 1:10. The column is packed with 14–30 or 30–60 mesh polyamide. Universal Factory of Shanghai, Garrison Command P.L.A. The polyamide is packed in a 95% alcohol solution and then equilibrated with 5% aqueous alcohol solution. The column is then washed with gradient elution of aqueous ethanol mobile phase (from 5% to 95%) followed by deionized water. More specifically, the centrifuge fluid is added to the column so that the ratio is approximately 0.7–10 g of raw material to 1 ml polyamide (or about equal to 0.27 g polyamide). The flow rate is approximately 3 times volume number (liters) of polyamide (unit: ml/min) (for example: when the volume of polyamide in column is 100 L, the velocity of flow is 300 ml/min). The column is eluted with the various concentrations of alcohol solution, for example:

| Eluting grade | 0% | 10% | 20% | 50% |
|---|---|---|---|---|
| Quantity of eluant (column volumes relative to polyamide) | 4 | 2 | 4 | 2 |

Applicants have discovered that by carefully controlling the percentage of alcohol in the eluant, one can recover the lactones separately from the flavone glycosides. This allows Applicants to subsequently re-combine the recovered lactones and recovered flavone glycosides to desired concentrations. Thus, the ability to craft the percentages in the combinations of recovered lactones and flavone glycosides permits one to create novel compositions in a deliberate and controlled manner. For example, the flavone glycosides are recovered in an alcohol solution ranging from approximately 20% to 70% which is combined and detected by HPLC in the manner described, for example, in section 6.6, infra. The recovery of flavones is generally more than 75%.

To obtain the lactones, the centrifuge fluid through the chromatography column is mixed in 5%, 10%, 15% and 20% alcohol fractions and concentrated to $^1/_{10}$ volume under reduced pressure. The lactones are extracted three times from the above concentrated solution with ethyl acetate, the ethyl acetate volume is 1, $^2/_3$ and $^1/_3$ of concentrated aqueous solution volume, respectively. Specifically, each extraction is stirred for about 10–15 minutes and mixed with the ethyl acetate solution. Water is removed with the addition of anhydrous sodium sulfate. Alternatively, the lactones may be extracted by the countercurrent liquid-liquid extraction method with ethyl acetate and concentrated solution. The quantity is approximately 1:1 aqueous solution. The length of the extracting column to the diameter of the extract column is 800:15. The ethyl acetate is removed under reduced pressure and the residue is dissolved with a 95% alcohol solution. The desired concentration of lactones and flavone glycosides are then mixed.

There are two separate solutions each containing the bioactive principles. One is the flavone glycoside solution (eluted off polyamide with 20–70% alcohol, the other is lactone part (extracted with ethyl acetate). These solutions are combined in proportions to create, for example, a 24/6 or 27/7 or 30/7 mixture. This ratio is confirmed by HPLC. If desired, in order to enhance the ratios of terpene lactones, prior to the combining described above, the terpene lactone mixture can be further treated by chromatography on a macroporous resin. The terpene lactones are preferentially adsorbed onto a macroporous resin in dilute aqueous methanol. Ginkgolides A & B are preferentially absorbed over C & bilobolibe. Macroporous resins, such as, but not limited to, YPR-II, HP-20 (Mitsubishi) strongly adsorb ginkgolide A and B. These terpene lactones are eluted with increasing concentration of alcohol in aqueous alcohol solutions. Additionally, as described below in Section 5.5.2., the use of the macroporous resins eliminates the need to remove the ginkgolic acids, which are retained in the column, such as described in Section 5.6.

2. Macroporous Hydrophobic Resins

In the alternative to doing column chromatography using polyamide as described in Section 5.5.1, macroporous hydrophobic resins, such as, but not limited to, ADS-17 (Tianjing), DM-130 (Shangdong) or HP-20 (Mitsubishi Chemical) may be used. Applicants have discovered that under certain conditions these resins, particularly DN-130 and HP-20, permit not only the separation and excellent yield of flavones and lactones, but further substantially reduces the content of ginkgolic acids. Thus, for example, the additional steps described in section 5.6, infra, are unnecessary. An additional benefit is that the percentage of lactones may be further enhanced by simply repeating the chromatography by eluting with increasing concentrations of alcohol in aqueous alcohol solutions. The ratio of the diameter to the length of the column is approximately 1:10. A gradient of eluent of 10%, 20% and 30% of alcohol solution, for example, may be used. The flavone glycosides are eluted in a gradient of about 40–70% alcohol solution for example. The excellent retention of the ginkgolic acids eliminates the need to perform the steps described in Section 5.6., below.

E. REMOVING THE GINKGOLIC ACIDS

When desired, ginkgolic acids may be removed from the aqueous concentrate containing the flavones and lactones by diluting with water and ethanol, so that a solution with 10% dry weight extract in 30% aqueous weight ethanol is obtained. To reduce the ginkgolic acids to a residual content of less than 5 ppm, this solution is stirred at least four times at room temperature, each time with one-third of its volume of n-hexane, cyclohexane or petroleum ether. Alternatively, the countercurrent liquid-liquid extraction method may be used to remove the ginkgolic acids by using an equal volume of n-hexane or cyclohexane. The aqueous solution is then concentrated under reduced pressure to yield a high-density fluid extract and spray dried or vacuum dried to a dry extract with a water content of less than 3 weight percent. Preferably, however, hexane is not used, and the ginkgolic acids (alkylphenols) are removed during chromatography as described above.

The term "lactones" or "terpene lactones" as used herein, refers to both the ginkgolide and bilobalide content.

It has been discovered that the ratio of the amount of ginkgolide B to the sum of the amounts of ginkgolide A and ginkgolide C in extracts produced according to the invention can be controlled within the range from about 1.4:5 to about 1.6:5, preferably about 1.5:6 to about 1.5:7, more preferably about 1.4:6 to about 1.6:6. The increased proportion of ginkgolide B affords improved bioavailability.

The present invention is not to be limited in scope by the examples disclosed since these embodiments are intended as illustrations of various aspects of the invention. Any embodiment which is functionally equivalent to that described is within the scope of this invention. Indeed, various modifications of the invention, in addition to those shown and described herein, will become apparent to those skilled in the art from the foregoing description. Such modifications are intended to fall within the scope of the appended claims.

EXAMPLE

Process for Obtaining GBE 27/7

This process is a method for producing extracts of *Ginkgo biloba* leaves (GBE 27/7) containing 27 weight percent flavone glycosides and 7 weight percent of lactones, and in particular, containing ginkgolide B that is more than 1.45 weight percent.

Green leaves were selected during the period of August to September from the Shandong region of China. The green leaves were dried and combined.

In order to control the water content in the leaves, 100 g of green leaves were dried to a constant weight in a water detector Kangle DZF-1 model. The content of water in leaves was then calculated based on drying to constant weight.

In order to detect the active constituents, 100 g of the leaves were crushed to 10–20 mesh powder. 800 ml of a 50% alcohol solution was then added and refluxed for 2 hours in a Universal extractor. The crushed leaves are then filtered to 120 Mesh. A second extraction was done with 600 ml of a 50% alcohol solution and was then added to the solid residue and refluxed for 1 hour and then filtered. The third extraction was the same as the second extraction. The three filtered solutions were combined and concentrated under a reduced pressure 0.08–0.09 MPa at 70° C. to dry the extract. HPLC analysis was then performed to determine the content of total flavone glycosides in the crude extract.

100 Kg of the green Ginkgo B. L. leaves found to have a total glycoside content of about 4 percent weight were crushed to 10–20 mesh powder, 800 liters 50% alcohol solution was added and poured into a universal extractor and refluxed for 2 hours. The leaves were then filtered to 120 mesh. The residue was then subjected to a second extraction with 600 liters 50% alcohol solution under the same conditions for 1 hour and then filtered. A third extraction was performed in the same way as the second. The three filtered solutions were then combined. The organic solvent was separated from the above filtration solution and then concentrated by evaporation under reduced pressure to form a high-density fluid extract (D=1.2–1.25 g/cm$^3$).

The high-density fluid extract was diluted with 200–300 liters boiling water. The solution was kept boiling and stirred constantly for about 20 minutes. The solution was then precipitated for about 24 hours at room temperature. The water-insoluble lipophilic components were removed from the diluted aqueous solution by high speed tubular centrifuge (rotary speed 16,000–20,000 r/min) for about 5 hours Model GQ-105 tubular centrifuge.

Column chromatography was performed using a stainless steel column where the ratio of the diameter of column to the length of column was approximately 1:10. The column was 30–60 mesh polyamide. The polyamide was packed in a 95% alcohol solution. The column was then washed with deionized water followed by gradient elution with aqueous ethanol mobile phase (from 5% to 75%). 3000 ml centrifuge fluid was added to 1000 ml polyamide (about equal to 270 g polyamide). The flow rate was approximately 3 times volume number (liters) of polyamide (unit: ml/min) (for example: when the volume of polyamide in column was 100 L, the velocity of flow is 300 ml/min).

The flavone glycosides were recovered in a 50% alcohol solution from a combination of 20% to 70% alcohol solution which was then combined, and detected by HPLC using a Waters Nova-pak™ C$_{18}$ 3.9×150 mm column with an 0.04% phosphoric acid-methanol (51:49) eluent at a flow rate of 1 ml/min. UV detection was at 260 nm. Quantitation was performed by HPLC. Retention time in minutes was 4.805, 8.588 and 9.788 for Quercetin, Kaempferol and Isorhamnetin, respectively.

To obtain the lactones, the centrifuge fluid was mixed through the chromatography column in 5%, 10%, 15% and 20% alcohol fractions and concentrated to ⅒ volume under reduced pressure. The lactones were extracted by the countercurrent liquid-liquid method with ethyl acetate. Water was removed with the addition of anhydrous sodium sulfate, 1% weight/volume. The quantity was approximately 1:1 aqueous solution. The length of the extracting column to the diameter of the extract column is 800:15. The ethyl acetate was removed under reduced pressure and the residue was dissolved with a 95% alcohol solution. Detection by HPLC using a Hypersil ODS $C_{18}$ $5_u$, column with a water-methanol-tetrahydrofuran (75:20:10) eluent. Flow rate was 1 ml/min. Retention time was 9.867 for ginkgolide C, 11.233 for bilobalide, 14.317 for ginkgolide A and 18.500 for ginkgolide B with a Waters 410 differential refractometer detector. The desired concentration of lactones and flavone glycosides were then mixed.

In a typical example, beginning with 200 kg *Ginkgo biloba* leaves, a concentrate of lactones 1.6 kg was obtained. The content of lactones is 35%, and the flavone glycoside fraction of 2.3 kg contains 44% flavone glycosides. Combination of two fractions gave a combined extract of 3.9 kg, flavone glycosides 26%, and total terpene lactones 14.5%.

The resultant aqueous concentrate was diluted with water and ethanol, so that a solution with 10% dry weight extract in 30% aqueous weight ethanol was obtained. From 100 kg ginkgo leaves, 4.5 Liters of aqueous concentrate was obtained after removal of alcohol. This solution was diluted to a solution containing 10% dry weight extract in 30% aqueous alcohol. To reduce the ginkgolic acids to a residual content of less than 5 ppm, this solution was extracted at least four times at room temperature, each time with ⅓ of its volume of either n-hexane or cyclohexane, or using the countercurrent liquid-liquid extraction to remove off the ginkgolic acids with n-hexane. Then, the aqueous solution was concentrated under reduced pressure to high-density fluid extract, vacuum dried to a dry extract with a water content of less than 3 weight percent. HPLC chromatography of ginkgolic acid utilized a Waters Novapak™ $C_{18}$ 3.9×150 mm column with eluent A: acetonitrile; eluent B: 0.04% phosphoric acid at a flow rate of 1 ml/min. For example at 0–25 min., the ratio of A–B=75; 25–27 min. A=100 B=0; 27–30 min. A:B-100:0, 30.5 min. A=75 and B=25. UV detection was at 210 nm. Retention time (min.) was 19.127 for ginkgoneolic acid and 20.460 ginkgolic acid.

The final product was a light yellow powder and had a faint smell of *Ginkgo biloba* L. leaves. Content detection: the content of total flavonol glycosides was 27.0 weight percent. The content of total lactones was 7.69 weight percent. Notably, the content of ginkgolide B was 1.49 weight percent. The content of ginkgolic acid was less than 5 ppm.

The bioavailability of the ginkgolides in an extract prepared by the method of the invention was assessed. The extract was enriched for ginkgolide B and contained 27% w/w Ginkgo-flavone glycosides and 7% w/w terpene lactones (BioGinkgo 27/7) and was compared to that of a standardized commercially available, "24/6" extract. Ginkgolide levels were determined by using an assay based on their ability to inhibit the binding of platelet aggregation factor (PAF) to its receptor in vitro (Sticher, O. (1993) *Planta Med*. 59, 2–11; Hwang, S-B., Lee C-S, C. Cheah, M. J., Shen, T. Y. (1983) Biochemistry 22, 4756–4763).

More specifically, the bioavailability of ginkgolides in these extracts was assessed in rabbits which received either BioGinkgo 27/7, 40 mg/kg, BioGinkgo 27/7, 60 mg/kg, or control 24/6 extract, 40 mg/kg. It was found that after a single dose, as explained below, the extract of the invention resulted in a higher concentration of ginkgolides which was maintained over a longer period of time than was found with the commercial extract prepared by conventional methods.

The test and control samples of *Ginkgo biloba* extracts were prepared by grinding and homogenization of commercial tablets into a fine aqueous suspension. Analysis of the ginkgolide composition of the extracts by HPLC showed that the control 24/6 and BioGinkgo 27/7 extracts contained 0.87% w/w and 1.49% w/w ginkgolide B, respectively. The control extract contained 24.95% flavonoids and 6.09% terpene lactones and the BioGinkgo 27/7 contained 27.0% flavonoids and 7.69% terpene lactones.

Twenty four rabbits, 12 male and 12 female, (weight, 2.1±0.3 kg) were divided into three treatment groups (8 rabbits per group) and were administered a single oral dose of either BioGinkgo 27/7, 40 mg/kg, BioGinkgo 27/7, 60 mg/kg, or control 24/6 extract, 40 mg/kg. Blood samples were taken at 0.5, 1, 2, 3, 5, 8, and 12 hours after treatment. Plasma was prepared and by conventional methods. The plasma was stored −20° C. before analysis and was analyzed for ginkgolide content using the PAF receptor-binding inhibition assay.

Ginkgolides in serum were assayed by their ability to inhibit the binding of PAF to its platelet membrane receptor in vitro (Nenez, D., Chignard, M., Korth, R., LeCoouedic, J. P., Norel, X., Spinnewyn, B., Braquet, P., Beneveniste, J. (1986) *Fur, J. Pharmacol.*, 123, 197–205; Braquet, P., Drieu, K., Etienne, a. (1986) Actual. Chim. Ther. (Paris) 13, 237–254). The assay was carried out as described by Hwang et al. (Hwang, S-B., Lee C-S, C. Cheah, M. J., Shen, T. Y. (1983) *Biochemistry* 22, 4756–4763) using rabbit platelet membranes. The assay mixture contained: 380 µl platelet membrane suspension, 10 µl rabbit serum with reagent cocktail, and 10 µl $^3$H-PAF (0.1 µCi/µmole). Incubation was at 25° C. for 40 min. Free and bound $^3$H-PAF were separated by vacuum filtration through glass-fiber filters and the radioactivity in the dried filters determined. Inhibition of PAF binding to its platelet receptors by ginkgolides A. B, C, has been shown to be highly specific ($IC_{50}$ for ginkgolide B approximately $10^{-7}M$) (Nenez, D., Chignard, M., Korth, R., LeCoouedic, J. P., Norel, X., Spinnewyn, B., Braquet, P., Beneveniste, J. (1986) *Eur. J. Pharmacol*. 123, 197–205; Braquet, P., Drieu, K., Etienne, A. (1986) *Actual, Chim. Ther*. (Paris) 13, 237–254) and is not affected by other components of ginkgo extract (Stinke, B., Muller, B., Wagner, H. (1993) Planta Med., 59, 155–160). A standard curve was constructed by including known amounts of unlabeled PAF in blank serum at final concentrations between 0.025 and 250 µg/ml together with $^3$H-PAF in the receptor binding assay described above.

Results are expressed as the mean±standard deviation (SD). The significance of differences between means was assessed using Students t-test for unpaired values.

The data in FIG. 1 show that there was a significant and unexpected difference in the pharmacokineties of ginkgolides in the two extracts. With the control 24/6 extract, there was a single peak in the ginkgolide plasma concentration at 3 hr after treatment. In contrast, two peaks were seen after treatment with the BioGinkgo 27/7 extract: at 2 hr and 5 hr with the 40 mg/kg dose and at 1 hr and 5 hr with the 60 mg/kg dose. The peak plasma concentration obtained with BioGinkgo 27/7 dose of 60 mg/kg (25.1±3.39 µg/ml), indicates a dose-response relationship. The peak plasma concentrations obtained with BioGinkgo 27/7 and the control 24/6 extract at 40 mg/kg were similar, 18.8±1.97 and 17.8±0.59 µg/ml, respectively. Over the 12 hr treatment period, the ratios of the areas under the plasma concentration-time curves for the control 24/6 extract, 40 mg/kg,: BioGinkgo 27/7, 40 mg/kg,: BioGinkgo 27/7, 60 mg/kg, were 1:1.40:1.83, indicating a greater bioavailability of ginkgolides in the BioGinkgo 27/7 for a given dose of extract. This was also evidenced by the fact that, 12 hr after treatment at the 40 mg/kg dose level, the plasma ginkgolide level obtained with the BioGinkgo 27/7 was 2.6 fold greater than that seen with the control 24/6 extract, 13.2±0.38 µg/ml vs. 5.01±0.42 µg/ml, respectively.

Both the BioGinkgo 27/7 and control 24/6 extracts showed rapid absorption. The data obtained with the control extract are consistent with those reported by Moreau et al. (Moreau, J. P., Eck, J., McCabe, J., Skinner, S. (1986) *Presse Med*, 15, 1458–1461), who found a single peak in plasma specific activity after treating rats with radio-labeled Ginkgo extract. In contrast, in the present study the plasma concentration of ginkgolides from the BioGinkgo 27/7 was measured in the upper gastrointestinal tract, which has been shown to be a site of absorption of *Ginkgo biloba* extracts (Moreau, J. P., Eck, J., McCabe, J., Skinner, S. (1986) *Presse Med*, 15, 1458–1461). After treatment with the control 24/6 extract, the peak in ginkgolide plasma concentration occurred at 3 hr (FIG. 1), slightly later than the peak time of 1.5 hr reported by Moreau et al. (Moreau, J. P., Eck, J., McCabe, J., Skinner, S. (1986) *Presse Med*, 15, 1458–1461), which is believed to be due to a species difference in the rate of absorption between rats and rabbits. Peak concentrations were reached more rapidly with both the 40 mg/kg and 60 mg/kg doses of BioGinkgo 27/7 extract than with the control 24/6 extract. The prolonged and greater bioavailability of the ginkgolides in the BioGinkgo 27/7 prepared by the methods of the invention compared to the control 24/6 extract may be due to two factors: the higher terponoid content of the BioGinkgo 27/7 preparation and, more importantly, the fact that this extract is enriched for ginkgolide B, which has been shown to have a longer half-life in rats and in humans than ginkgolide A (Kleijnen, J., Knipschild, P. (1992) *Lancet* 340, 1136–1139.; Moreau, J. P., Eck, J., McCabe, J., Skinner, S. (1986) *Presse Med*, 15, 1458–1461). Thus, the method of preparation of the Ginkgo extracts of the invention has a marked effect on the bioavailability of the ginkgolides extracts (the ginkgolides being one of the therapeutically active constituents).

All references cited herein are incorporated herein in their entirety for all purposes unless otherwise noted.

What is claimed is:

1. A process for the production of an extract of improved biological property from the leaves of *Ginkgo biloba* comprising:
   (a) collecting green *Ginkgo biloba* leaves of a desirable quality;
   (b) treating the leaves with a 50% aqueous alcohol solution to obtain a crude extract;
   (c) filtering and concentrating the crude extract to a high density fluid extract;
   (d) diluting the high density fluid extract with boiling water to remove water-insoluble lipophilic compounds;
   (e) eluting the resultant extract through a chromatographic column with a gradient of aqueous alcohol to obtain a plurality of fractions containing flavone glycosides and a plurality of fractions containing lactones and to remove alkyl phenolic compounds;
   (f) combining a suitable number of the fractions containing flavone glycosides with fractions containing lactones to obtain a refined extract having a weight ratio between the flavone glycosides and the lactones of 24 to 6, about 27 to about 6–7, 27 to 7, or 30 to 7; and optionally
   (g) further treating the refined extract with a non-polar solvent to remove alkyl phenols.

2. The process of claim 1 wherein in Step (a) the leaves are collected from August to September from *Ginkgo biloba* trees that are about 3–5 years of age, dried and crushed to a pore size of about 5–20 mesh.

3. The process of claim 2, wherein in Step (c) the high density fluid extract is of a density of about 1.20–1.25 g/cm$^3$.

4. The process of claim 1 wherein in Step(e) the gradient aqueous alcohol solution is 20–70% for eluting the fractions containing flavone glycosides and 5–20% for eluting the lactone fractions.

5. The process of claim 1 wherein in Step(e) the fractions containing lactones are combined and further concentrated and extracted with ethyl acetate.

6. The process of claim 5 wherein the fractions containing lactones comprise Ginkgolide A, Ginkgolide B and Ginkgolide C.

7. The process of claim 6 wherein the weight ratio Ginkgolide B to the combined weight ratio Ginkgolides A and C is about 1.4%:5.0% to about 1.5%:7.0%.

8. The process of claim 1 wherein in Step(g) the alkyl phenols are removed by extracting with an organic solvent selected from the group consisting of hexane, cyclohexane and petroleum ether.

9. The process of claim 1 wherein in Step(d) the column is packed with a resin selected from a group consisting of a polyamide resin and a macroporous hydrophobic resin.

10. The process of claim 1 wherein in Step(f) the weight ratio between the flavone glycosides and the lactones is from about 27 to about 6–7 and the fractions containing lactones have a Ginkgolide B content of at least about 1.4%.

11. The process of claim 1 wherein in step g) the content of ginkgolic acids in said extract is less than about 5 ppm.

12. A process for the production of an extract from the leaves of *Ginkgo biloba* comprising the steps of:
   a) extracting fresh or dried leaves from *Ginkgo biloba* which are crushed to a pore size of about 5–20 mesh powder using an about 50% alcohol solution to yield a crude extract comprising at least about 5 wt % of flavone glycosides;
   b) filtering and concentrating said crude extract to a density of about 1.2 to 1.25 g/cm$^3$;
   c) diluting said concentrated crude extract with boiling water and precipitating said diluted extract for about 24–48 hours at about 10°–120 ° C.;
   d) removing water-insoluble lipophilic components from said diluted extract by high speed tubular centrifuge at a rotary speed of approximately 16,000–20,000 r/min;
   e) performing column chromatography on said centrifuged extract using a column packed with 14–30 or 30–60 mesh polyamide in about 95% alcohol solution;
   f) eluting said column with a gradient elution of an about 5% to an about 75% alcohol solution;
   g) obtaining lactones in the recovered 10–20% alcohol fractions by first concentrating said lactones, then extracting said lactones with ethyl acetate, and subsequently determining the concentration of the recovered lactones;
   h) obtaining flavone glycosides in the recovered 20–75% alcohol fractions and then determining the concentration of the recovered flavone glycosides;
   i) forming a combined extract by combining said recovered lactones and flavone glycosides to a selected concentration of each; and
   j) removing alkylphenol compounds from said combined extract to a residual content of less than about 5 ppm.

* * * * *